United States Patent [19]
Kuzma

[11] Patent Number: 5,645,585
[45] Date of Patent: Jul. 8, 1997

[54] COCHLEAR ELECTRODE IMPLANT ASSEMBLY WITH POSITIONING SYSTEM THEREFOR

[75] Inventor: Janusz A. Kuzma, Englewood, Colo.

[73] Assignee: Cochlear Ltd., Lane Cove, Australia

[21] Appl. No.: 616,299

[22] Filed: Mar. 15, 1996

[51] Int. Cl.$^6$ .................................. A61F 2/18; A61N 1/05
[52] U.S. Cl. .................................................. 623/10; 607/137
[58] Field of Search ............................... 607/137, 56, 57; 128/898; 156/245; 623/10

[56] References Cited

U.S. PATENT DOCUMENTS

| | | | |
|---|---|---|---|
| 4,284,085 | 8/1981 | Hansen et al. | 128/784 |
| 4,819,647 | 4/1989 | Byers et al. | 128/642 |
| 4,832,051 | 5/1989 | Jarvik et al. | 128/784 |
| 4,898,183 | 2/1990 | Kuzma | 128/784 |
| 5,000,194 | 3/1991 | van den Honert et al. | 128/784 |
| 5,037,497 | 8/1991 | Stypulkowski | 156/245 |
| 5,443,493 | 8/1995 | Byers et al. | 607/137 |

FOREIGN PATENT DOCUMENTS

| | | |
|---|---|---|
| 0002068 | 5/1979 | European Pat. Off. . |
| 0007157 | 1/1980 | European Pat. Off. . |
| 2823798 | 9/1979 | Germany . |

OTHER PUBLICATIONS

W. Bruszewski et al., "Injection Molded Structural Spine," 1994 RETEC:R94–034, pp. 2–20 and Figs. 1–12, Studies on Pediatric Auditory Prosthesis Implants, 15th Quarterly Progress Report, Apr. 1, 1994 to Jun. 30, 1994, from Coleman and Epstein Laboratories, University of California, San Francisco.

Kuzma et al., U.S. Pat. Appln. Ser. No. 08/211,269, "Self-Curving Cochlear Electrode Array," filed May 4, 1994.
Kuzma, U.S. Pat. Appln. Ser. No. 08/414,656, "Cochlear Electrode Implant Assemblies With Positioning System Therefor," filed Mar. 30, 1995.
Heller, U.S. Pat. Appln. Ser. No. 08/534,510, "Device and Method for Inserting a Flexible Element into Soft Tissue," filed Dec. 4, 1995.

*Primary Examiner*—Debra S. Brittingham
*Attorney, Agent, or Firm*—Gottlieb, Rackman & Reisman, p.C.

[57] ABSTRACT

An implantable cochlear electrode assembly includes a flexible rod-like electrode carrier and a flexible rod-like positioning member which are initially parallel to and closely alongside each other and, when the assembly is inserted endwise into the cochlea, adopt the spiral curvature of the cochlea. The electrode carrier and the positioning member are connected to each other at their respective leading end regions by a latchless rod-and-socket joint and at their respective trailing end regions by a ring-shaped member having a generally D-shaped cross-sectional configuration, with the flat wall of the "D" defining the circumferential boundary surface of the passageway in the ring member through which the electrode carrier and the positioning member jointly pass with a close fit. The medial regions of the electrode carrier and the positioning member are separate from and unconnected to each other, so that within the cochlea the positioning member can assume an outwardly arched configuration relative to the electrode carrier for forcing the latter into a close hugging engagement with the modiolus and for disposing the contact faces of the electrodes in as close a juxtaposition to the cells of the spiral ganglion as possible. The latchless rod-and-socket joint enables the positioning member to be withdrawn from the assembly without disturbing the electrode carrier.

7 Claims, 3 Drawing Sheets

COCHLEAR ELECTRODE IMPLANT ASSEMBLY WITH POSITIONING SYSTEM THEREFOR

This invention relates to cochlear electrode implant assemblies, and more particularly to a system for optimally positioning an implanted stimulating electrode assembly including an array of electrodes on a carrier therefor in the cochlea of a human ear.

CROSS REFERENCE TO RELATED APPLICATION

The present invention is an improvement over the cochlear electrode implants and in particular over the cochlear electrode positioning systems disclosed in my prior copending U.S. patent application Ser. No. 414,656 filed Mar. 30, 1995 and entitled "Cochlear Electrode Implant Assemblies With Positioning System Therefor."

BACKGROUND OF THE INVENTION

Generally speaking, the portions and structural components of a human ear with which both the present invention and the invention disclosed in the aforesaid prior application are most closely concerned, are well known to those skilled in the art. Since the basic ear structure and its manner of functioning, as well as the basic structural configurations of a number of known cochlear electrode implants previously designed to overcome the effects of sensorineural hearing loss, are fully described and illustrated in my prior application, the entire introductory and background portion of the disclosure of the said prior application is incorporated in the present application by this reference.

The cochlear electrode implant assemblies disclosed in my prior application were designed, through the provision of a separately curvable auxiliary positioning member connected at its leading and trailing end regions to the corresponding end regions of the electrode carrier, to enable the electrode carrier of such a cochlear electrode implant assembly to be positioned optimally in the cochlea of a human ear, that is to say, so as to ensure that in the fully implanted state of the assembly, the electrical contact elements or electrodes are located in the closest possible proximity to the modiolus and the ganglion cells. In conjunction therewith, the means by which the electrode carrier and the auxiliary positioning member of an implant assembly according to my prior invention are connected to each other were designed also to lock the assembly in place within the cochlea at the end of the insertion stage so as to firmly and stably secure the assembly against movement in and withdrawal from the cochlea.

Given the structural and functional characteristics of the means disclosed in my prior application for connecting the electrode carrier of the implant assembly to the associated positioning member at their respective leading and trailing end regions, however, it can be seen that a removal of the implanted assembly or a part thereof from the patient's ear, should that become necessary or advisable (for example, for purposes of repair and/or replacement or for allowing a diagnostic or surgical procedure to be performed on or in the patient's ear), is very difficult to achieve and may even be impossible without a destruction of the implant assembly.

BRIEF DESCRIPTION OF THE INVENTION

It is an object of the present invention, therefore, to provide a cochlear electrode positioning system of the general type disclosed in my prior application but which incorporates a modified construction of the means for connecting the positioning member and the electrode carrier to each other so as to permit the positioning member to be withdrawn from the patient's ear easily and separately from and without disturbing the electrode carrier, thereby to facilitate a subsequent extraction of the electrode carrier if that should become desirable or necessary.

Generally speaking, in the implant assembly according to the present invention the initially straight rod-like flexible electrode carrier, to which the multiple electrode elements or contacts (which may be as many as 22 or more in number) are secured in any desired way, is combined, as before, with an initially straight rod-like flexible positioning member which extends along the length of the electrode carrier and has a leading end region and a trailing end region connected to the leading end region and the trailing end region, respectively, of the electrode carrier in a manner to be more fully discussed hereinafter. In the assembly of the present invention, the electrode carrier and the positioning member are both in the form of solid rods and are made throughout of respective biocompatible flexible plastic materials. Preferably, the electrode carrier is made of a flexible biocompatible silicone polymer such as Silastic. On the other hand, the positioning member preferably is made from a somewhat harder but still flexible biocompatible polymeric material such as nylon or Teflon (Teflon is a trademark for a material generically known as polytetrafluoroethylene or PTFE) or the like, which apart from having anti-friction properties also has a greater degree of stiffness and tensile strength than Silastic for enabling the positioning member to be used to pull the electrode carrier through the cochlea. The materials of which the electrode carrier and the positioning member in this embodiment of the present invention are made of must, of course, be such that they will not expand or swell upon being exposed to the water in the patient's body fluids.

The electrodes may be in the form of discrete layers or bands secured to and overlying respective full-circumference or part-circumference regions of the rod-shaped electrode carrier, or in the form of discrete either planar or dome-shaped layers or other formations, arranged on a carrier of either circular or part-circular or similar cross-section, but in all cases located generally at that surface (hereinafter occasionally referred to as the lower surface) of the electrode carrier which, upon insertion of the carrier into the cochlea, will be concavely curved toward the modiolus. In the assembly, the positioning member has its lower surface disposed adjacent that surface (the upper surface) of the electrode carrier which, upon insertion of the carrier into the cochlea, will be convexly curved away from the modiolus.

In the preferred embodiment of the present invention, the means for connecting the leading end region of the positioning member to the leading end region of the electrode carrier is a latchless rod-and-socket type of joint, while the means for connecting the trailing end region of the positioning member to the trailing end region of the electrode carrier is a ring-shaped member or band which is made of Silastic or the like and formed to be devoid of any sharp cutting edges. The ring defines a single interior passageway through which both the positioning member and the electrode carrier jointly extend with a close fit. The arrangement, which will be more fully described presently, is such that prior to the assembly (composed of the electrode carrier and the positioning member) being inserted into the scala tympani of the cochlea, both the electrode carrier and the positioning member, as in my prior invention, are in their starting straight and substantially parallel state, with the medial region of the positioning member between its leading and trailing end regions being separated from (in the sense of being unconnected to) the juxtaposed medial region of the electrode carrier.

The insertion of the assembly into the patient's ear is preferably effected by the surgeon gripping and pushing the positioning member forwardly with the aid of a suitable insertion tool. That action, by virtue of the interconnected leading end regions of the electrode carrier and the positioning member, causes the electrode carrier to be effectively pulled into the cochlea. When the assembly reaches and enters into the spiral curvature section of the cochlea, the positioning member comes with its upper or outwardly directed surface up against and rides along the radially outer wall of the cochlea within the scala tympani, while concurrently therewith the electrode carrier comes with a medial section of its electrode-bearing lower or inwardly directed surface up against the proximate initial region of the radially inner or modiolar wall of the cochlea.

Thereupon, the continuing pushing force being exerted by the surgeon on the positioning member causes the trailing end region of the latter to advance somewhat relative to the trailing end region of the electrode carrier past the location of the connection between the two trailing end regions, as the forward motion of the electrode carrier is retarded somewhat due to the frictional drag exerted by the modiolar wall on the electrode carrier. By virtue of the interconnections of the leading and trailing end regions of the electrode carrier with the leading and trailing end regions of the positioning member, this advance of the positioning member relative to the electrode carrier results on the one hand in the medial region of the positioning member between its leading and trailing end regions assuming an outwardly bowed or arched configuration relative to the medial region of the electrode carrier and on the other hand in the leading end region of the positioning member curving away from the outer wall and toward the radially inner wall of the cochlea. The tip of the electrode carrier thus is forced across the width of the scala tympani until the leading end region as well as substantially the entire length of the electrode-bearing surface of the electrode carrier up to the trailing end region thereof is in close hugging contact with the modiolar wall. Upon completion of the insertion, therefore, the electrodes supported by the electrode carrier are then held by the positioning member, due to the latter being outwardly bowed or arched relative to the electrode carrier against the constraint of the radially outer wall of the cochlea, in as close a juxtaposition to the ganglion cells as possible.

Once the electrode carrier has been fully advanced in this manner to the desired final arched state thereof, the entire assembly remains firmly in place, because in the absence of a rearwardly directed pulling force exerted on the positioning member, the arched portion of the positioning member, despite its being made of a material with anti-friction properties, is frictionally restrained by the ring member against reverse movement through the latter and hence is unable to straighten out. The positioning member thus remains in full surface contact over a major portion of its length with the radially outer wall of the cochlea. This stabilizes the assembly in the scala tympani and makes any inadvertent movement of the electrode carrier in the cochlea and especially a reverse movement thereof out of the cochlea effectively impossible.

The two parts of the assembly in this embodiment of the invention are connected to one another at their respective leading ends, as previously mentioned, by a latchless rod-and-socket type of joint, of which the rod-part is supported by the positioning member and the correspondingly configured socket-part is supported by the electrode carrier. In the currently contemplated best mode of implementing the joint, the socket-part thereof is constituted by a small tubular wire coil formation preferably utilizing a bundle of about 2–4 insulated wires which are identical to the conductors for the electrodes and are embedded in the electrode carrier at the time of its manufacture but are not connected to the signal source. Alternatively, of course, the coil formation can be made of a single somewhat thicker wire. The tubular wire coil formation is embedded in the tip end region of the electrode carrier so that the axial hollow interior of the coil slants forwardly somewhat in the direction from the upper surface of the electrode carrier toward the lower surface thereof, with the interior of the coil being accessible through an appropriate opening provided in the upper surface of the electrode carrier in axial alignment with the coil formation.

Correspondingly, the rod-part of the joint is constituted by the leading end region of a single guide wire running longitudinally through the positioning member. The said leading end region of this wire is of conventionally round cross-section, has a diameter of about 0.1 mm and a length of about 2 mm, and protrudes obliquely downwardly from the tip of the positioning member so as to be adapted to be slidably received in the hollow interior of the coil formation within the electrode carrier. The remainder of the guide wire is preferably flattened into a generally rectangular cross-section, has a thickness of about 0.03 mm and a width of approximately one half of the width of the positioning member, and extends through the entire length of the positioning member. The guide wire has a flat face thereof facing toward the electrode carrier, so that the guide wire serves as a stiffening element which renders the positioning member resistant to side to side flexure in the plane of the guide wire while permitting essentially unhindered flexure of the positioning member in a direction perpendicular to that plane, i.e., in the direction toward and away from the electrode carrier.

The currently preferred means for ensuring that the assembly according to the present invention remains locked in place in any given adjusted state of the assembly in the patient's ear is a fitting having a body made of a biocompatible plastic material such as Silastic and having the form of a ring or band of a generally D-shaped cross-sectional configuration, with the flat wall of the "D" defining the inner circumferential boundary surface of the ring. The inner configuration of the ring closely matches the combined outer configuration of the assembled electrode carrier and positioning member. Thus, when the positioning member and the electrode carrier are in their properly assembled state, the ring closely surrounds and embraces them at their trailing end regions and there connects them to each other. It will be understood that although the positioning member is made of a material (PTFE or the like) having anti-friction properties, in the absence of any longitudinal force applied by the surgeon to the positioning member the Silastic ring frictionally restrains the positioning member against any free or unforced longitudinal displacement through the ring and relative to the electrode carrier.

On the other hand, the anti-friction property of the material of which the positioning member is made ensures that when a longitudinal force is applied by the surgeon to the positioning member, the latter can slide through the ring and relative to the electrode carrier. Thus, when the surgeon, while the leading end regions of the positioning member and the electrode carrier are connected to each other by the interfitted parts of the latchless rod-and-socket joint, exerts (whether by hand or with the aid of a conventional insertion tool) a sufficient longitudinal forwardly directed pushing force on the positioning member rearwardly of the location where the trailing end regions of the positioning member and the electrode carrier are connected to each other by the ring, the positioning member is able to slide through the ring. As a result thereof, the portion of the positioning member located between the two connections, i.e., the portion between the ring and the rod-and-socket joint, assumes an outwardly arched or bowed configuration relative to the upper surface of the electrode carrier, so that by virtue of the upper surface of the positioning member coming into engagement with the radially outer wall of the cochlea, the electrode carrier is displaced across the width of the scala tympani so as to bring the contact elements on the lower surface of the electrode carrier into the closest possible proximity to the modiolus and the ganglion cells. Likewise as a result of the arching of the positioning member, the oblique orientation, relative to the axis of the ring, of that portion of the positioning member which is proximate to the ring in the region between the two connecting means, aided by the frictional contact between the ring and both the positioning member and the electrode carrier, ensures that the positioning member cannot of its own accord slide rearwardly through the ring and that the entire assembly will remain stable in its inserted position within the cochlea.

The anti-friction character of PTFE also comes into play when the implanted electrode assembly is to be extracted from the patient's ear. Should that become necessary for any reason, the surgeon, while holding the ring stationary in the patient's outer ear, will first exert on the positioning member a rearwardly directed longitudinal pulling force of sufficient magnitude to overcome the frictional interaction between the ring and the positioning member. This will cause a rearward sliding of the positioning member through the ring accompanied initially by a straightening of the arched portion of the positioning member while the electrode carrier remains in place. Ultimately, the rod-part of the joint between the leading end regions of the positioning member and the electrode carrier, which is not latched or locked to the wire coil formation in any way, will be pulled slidingly out of the associated socket-part of the joint to permit the positioning member to be fully withdrawn from the cochlea. What happens to the electrode carrier after such an extraction of the positioning member is dependent on whether or not scar tissue will have grown in the cochlea and encapsulated the electrode carrier. If encapsulation has taken place, the electrode carrier will be held in place by the scar tissue that has grown around it and will remain in its operational adjusted position, with the electrodes or contact elements in close proximity to the modiolus. If no encapsulation has taken place, the "memory" of the material of which the electrode carrier is made will cause the latter to try to return to its original straight form, which will leave the electrode carrier partially uncoiled and with its upper surface bearing against the radially outer wall of the cochlea. In either condition, of course, the electrode carrier can be relatively easily extracted from the cochlea.

BRIEF DESCRIPTION OF THE DRAWINGS

The foregoing and other objects, characteristics and advantages of the present invention will be more clearly understood from the following detailed description thereof when read in conjunction with the accompanying drawings, which are basically schematic or diagrammatic in nature and should be viewed as such, in which.

DETAILED DESCRIPTION OF THE INVENTION

Figure 1:
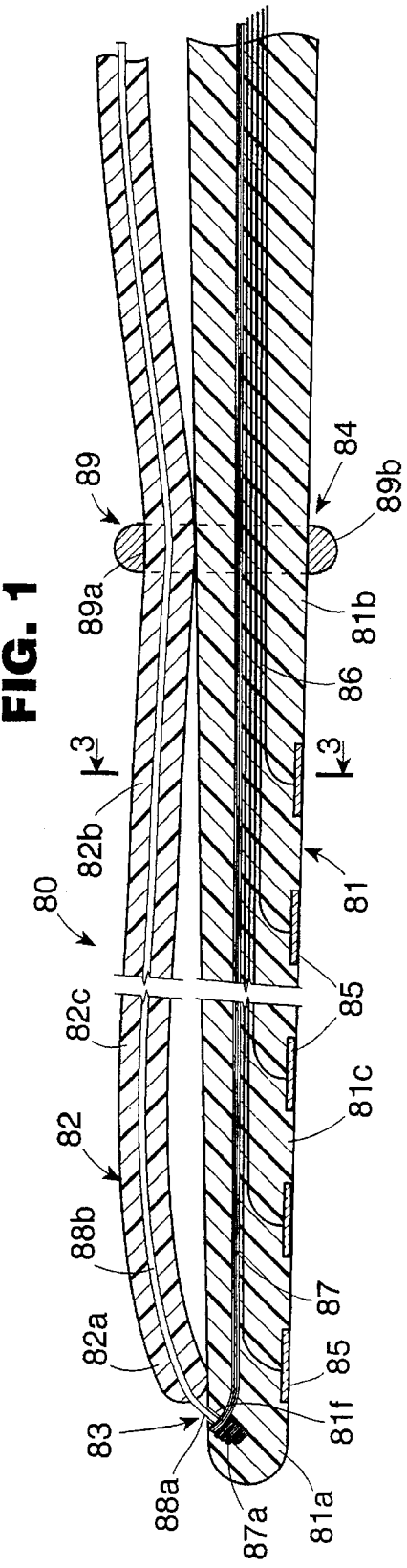
FIG. 1 is a fragmentary longitudinal sectional view of a cochlear electrode carrier/positioning member assembly according to the present invention essentially in the pre-insertion state of the assembly and illustrates a latchless rod-and-socket joint for interconnecting the leading end regions of the electrode carrier and the positioning member and a ring-shaped member for interconnecting the trailing end regions of the electrode carrier and the positioning member.
Figure 2:
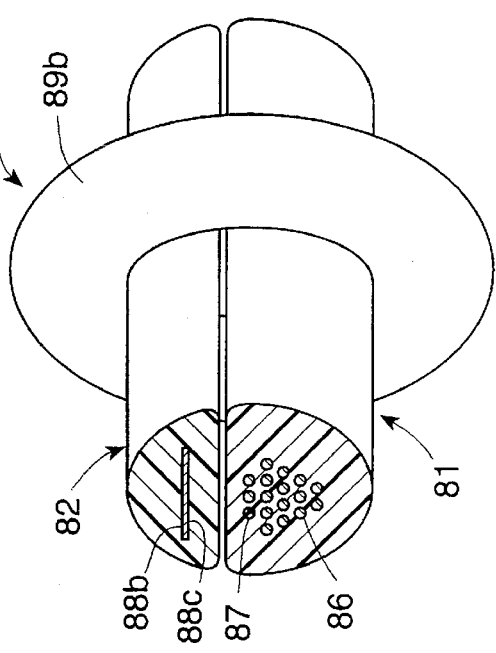
FIG. 2 is a perspective illustration, drawn to an enlarged scale, of the portion of the assembly of FIG. 1 in the region of the interconnection between the trailing end regions of the positioning member and the electrode carrier by the ring-shaped member.
Figure 3:
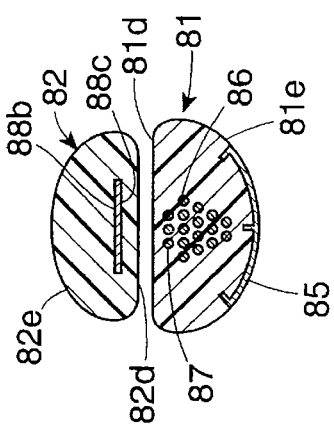
FIG. 3 is a sectional view taken along the line 3—3 in FIG. 1.

Referring now to the drawings in greater detail, FIGS. 1–3 show a cochlear electrode implant assembly 80 which, in accordance with the present invention, includes an electrode carrier 81 and an associated positioning member 82, together with means 83 for connecting the leading end region 81a of the electrode carrier to the leading end region 82a of the positioning member and with means 84 for connecting the trailing end region 81b of the electrode carrier to the trailing end region 82b of the positioning member while leaving the respective medial regions 81c and 82c of the electrode carrier and the positioning member separate from, i.e., unconnected to, each other. The electrode carrier 81 is shown as being a straight flexible solid rod of part-circular or semi-cylindrical cross-section having a flat upper surface 81d and an arcuate, preferably circularly curved, lower surface 81e, the rod being made of Silastic (a trademark for a commercially available silicone polymer) or an equivalent biocompatible material. The electrode carrier, in its medial region 81c between the leading and trailing end regions 81a and 81b, bears on its lower surface 81e an array of longitudinally spaced electrode elements 85 in the form of arcuate bands or layers of a biocompatible metal such as platinum or platinum alloy, and is further provided with a series of insulated electrical conductors 86 made of like biocompatible metals and embedded in the interior of the electrode carrier for conducting stimuli in the form of electrical sound-representing signals or impulses to the various electrode elements.

Correspondingly, the positioning member 82 in this embodiment of the invention is also a flexible solid rod of preferably part-circular or semi-cylindrical cross-section having a flat lower surface 82d and an arcuate, preferably circularly curved, upper surface 82e, this rod being shown as being somewhat thinner than the electrode carrier 81 (although this is not an essential or indispensable condition). The positioning member 82 initially is also generally straight, has its flat lower surface 82d juxtaposed to the flat upper surface 81d of the electrode carrier, i.e., to the side region of the latter opposite to the one where the contact faces of the electrode elements 85 are exposed, and extends lengthwise of and along the electrode carrier so as to have its leading and trailing end regions 82a and 82b adjacent, respectively, to the leading and trailing end regions 81a and 81b of the electrode carrier. The positioning member, for purposes of enhanced stiffness and tensile strength, is preferably made of a biocompatible material which is somewhat harder than Silastic, for example, nylon, Teflon (polytetrafluoroethylene) or a Teflon-like material, or the like.

It will be understood, of course, that the electrode carrier and the positioning member may have otherwise matching configurations, for example, the former may be of cylindrical cross-section and the latter of a crescent or moon-shaped cross-section, while the contacts or electrode elements may just as well have any of the configurations shown in my prior application Ser. No. 414,656.

Figure 5:
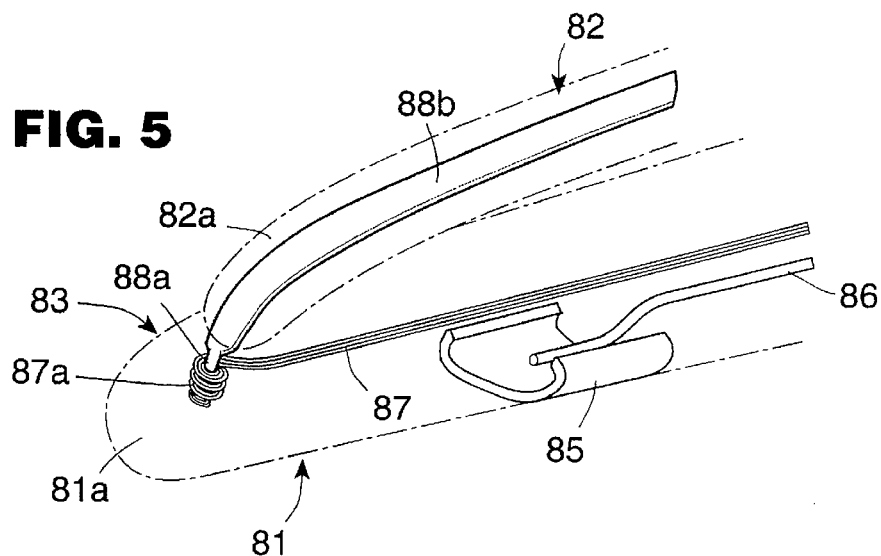
FIG. 5 is a perspective illustration, drawn to a somewhat enlarged scale, of the leading end region of the cochlear electrode implant assembly of FIG. 1.

The connection 83 between the leading end region 82a of the positioning member and the leading end region 81a of the electrode carrier in the illustrated embodiment of the present invention is effected, as best shown in FIGS. 1 and 5, by means of a latchless rod-and-socket joint which includes a socket-part supported by the electrode carrier and a rod-part supported by the positioning member.

Figure 4:
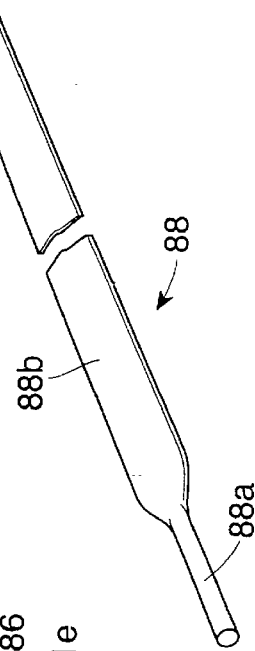
FIG. 4 is a perspective illustration of the guide wire for the positioning member of the assembly and shows the guide wire as having a cross-sectionally round front end portion to constitute the rod-part of the joint between the leading end regions of the positioning member and the electrode carrier and as having a generally planar or flat body portion for stiffening the positioning member.

More particularly, the electrode carrier 81 at the time of its manufacture is provided in its interior with a few, preferably from 2 to 4, additional insulated wires 87 (although one somewhat thicker wire could serve the purpose just as well) which are physically identical to and extend longitudinally through the electrode carrier like the conductors 86 but are not connected to the source of the electrical stimuli. The bundled wires 87 at their distal ends are arranged in a tubular coil formation 87a which is embedded in the tip region of the electrode carrier so as to have its axis or hollow interior slanting downwardly and forwardly from the flat upper surface 81d of the electrode carrier toward but not all the way to the arcuate lower surface 81e thereof. Access to the interior of the wire coil formation is provided through an opening or port 81f which is formed in the upper surface 81d of the electrode carrier and has its axis aligned with the axis of the coil formation 87a. Correspondingly, the positioning member 82 is provided at the time of its manufacture with an interior guide wire 88 (see FIG. 4) which extends along the entire length of the positioning member (see FIG. 1) and has its front end portion 88a projecting from the tip of the positioning member (see also FIG. 5). The front end portion 88a of the guide wire 88 is conventionally cross-sectionally round, having a diameter of about 0.1 mm, and projects for a distance of about 2 mm from the tip of the positioning member at an inclination to the longitudinal axis of the positioning member essentially matching the inclination of the axis of the coil formation 87a to the longitudinal axis of the electrode carrier. The main portion 88b of the guide wire 88, on the other hand, is flattened to a generally rectangular cross-section having a thickness of about 0.03 mm, and is disposed with its flat lower face 88c parallel to the flat lower surface 82d of the positioning member (see FIGS. 2 and 3). The portion 88b of the guide wire 88, with a width about half that of the positioning member, thus serves to stiffen the latter against flexure in the plane of the guide wire while permitting essentially unhindered flexure in a direction perpendicular to the plane of the guide wire, i.e., toward and away from the flat upper surface 81d of the electrode carrier.

It will be understood, therefore, that the wire coil formation 87a in the electrode carrier constitutes the socket-part of the joint or connection 83, while the end portion 88a of the guide wire 88 projecting from the positioning member constitutes the rod-part of the joint. Moreover, in order to establish the joint during the assembly of the positioning member and the electrode carrier with each other, it is merely necessary to slip the projecting rod-shaped end portion 88a of the guide wire 88 into the coil formation 87a through the opening 81f in the upper surface 81d of the electrode carrier. It will also be apparent from the foregoing description that the joint 83 is devoid of any device for latching or locking the rod-part 88a to the socket-part 87a. Thus, a positive connection between the electrode carrier and the positioning member exists only when the latter is moving longitudinally forwardly while the rod-part 88a of the joint is freely slidingly received within the hollow interior of the socket-part 87a of the joint, in other words, during the insertion of the assembly into the cochlea. When the positioning member is moved longitudinally rearwardly relative to the electrode carrier, the joint is automatically disabled as the rod-part 88a thereof, not being latched to the socket-part 87a, simply slips out of the socket-part and leaves the electrode carrier in place.

The connection 84 between the trailing end region 81b of the electrode carrier and the trailing end region 82b of the positioning member is effected by means of a fitting in the form of a ring-shaped band or like member 89 having an essentially D-shaped cross-sectional configuration characterized by a flat or planar inner wall 89a and an arcuate outer wall 89b, with the flat wall 89a of the "D" defining the inner circumferential boundary surface of the ring. As can be seen from FIGS. 1 and 2, the inner configuration (form and diameter) of the ring member 89 closely matches the combined outer cross-sectional configuration of the assembly constituted by the electrode carrier 81 and the positioning member 82 regardless of their individual cross-sectional configurations so that, in their properly assembled state, the ring closely surrounds and embraces the trailing end regions of the positioning member and the electrode carrier and, despite the anti-friction properties of the material (PTFE or the like) of which the positioning member is made, frictionally holds the electrode carrier and the positioning member together. That frictional engagement, therefore, especially when the portion of the trailing end region 82b of the positioning member located just forwardly of the connection 84 is (see FIG. 1) disposed at an obliquely upward inclination to the electrode carrier and in the absence of any externally longitudinally applied force acting on the positioning member, suffices to restrain the positioning member against any free longitudinal displacement thereof through the ring and relative to the electrode carrier. The anti-friction properties of the material of which the positioning member is made at the same time ensure that when a longitudinal rearwardly directed force of an appropriate magnitude is exerted on the positioning member, the oblique portion of the latter located forwardly of the ring will be able to straighten out and slide through the ring relative to the electrode carrier.

Figure 6:
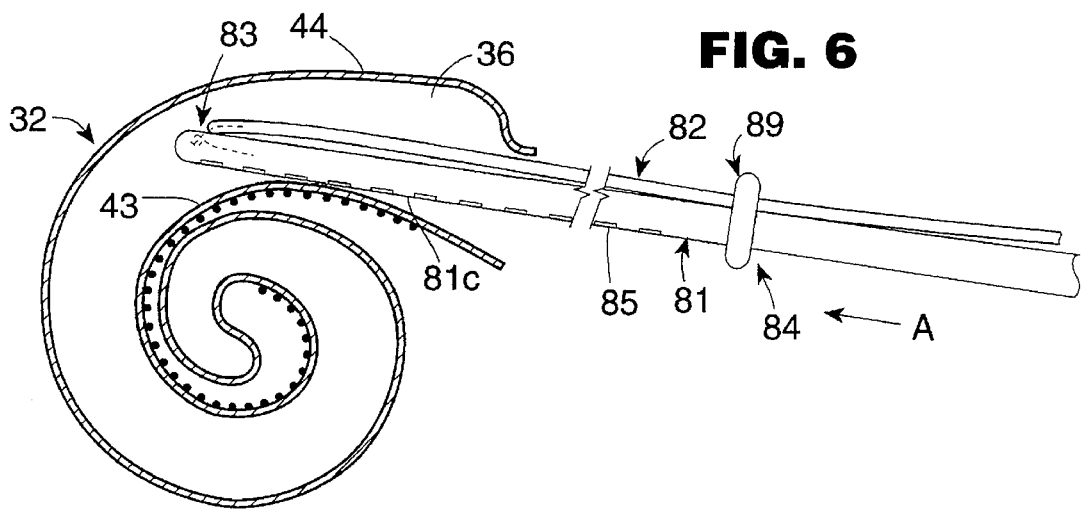
FIGS. 6, 7 and 8 are schematic illustrations, in longitudinal section, of, respectively, the initial, intermediate and final stages of the insertion of a cochlear electrode carrier and positioning member assembly according to the present invention into the cochlea of a human ear, with FIG. 8 showing the satisfactory final locked position of the electrode carrier.
Figure 7:
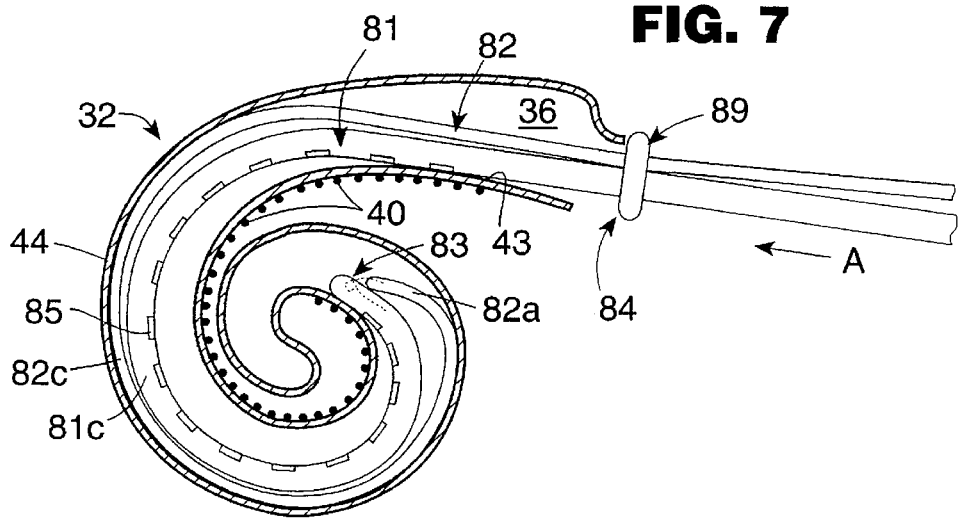
Figure 8:
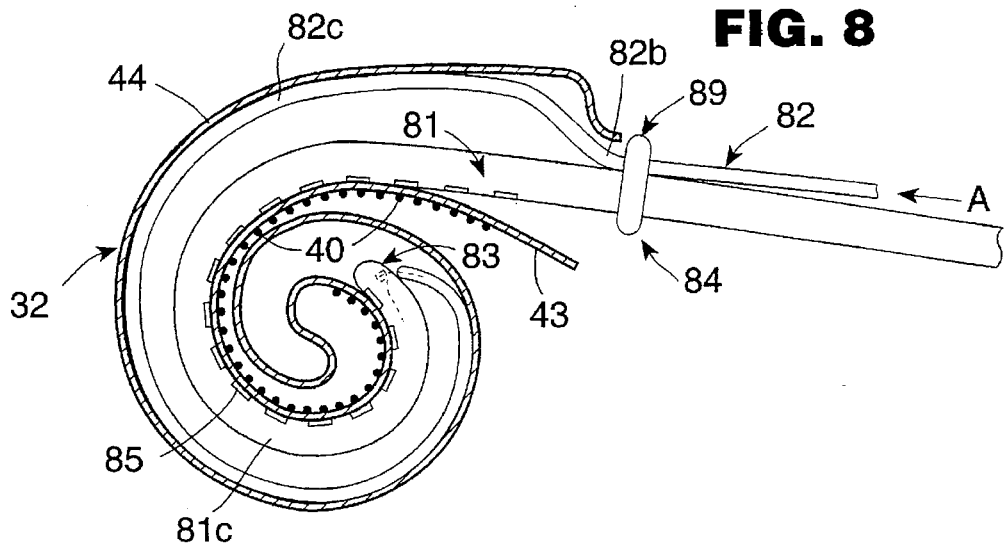

Referring now to FIGS. 6–8, in the initial phase of the implantation of the electrode carrier/positioning member assembly 80 into the cochlea 32, the leading end region of the assembly in its straight state is inserted into the scala tympani 36 of the cochlea in the usual way (see FIG. 6), with the side region, i.e., the lower surface, of the electrode carrier 81 where the contact faces of the electrodes 85 are exposed being directed toward the radially inner wall 43 of the cochlea and with the positioning member 82 lying at and along the side region, i.e., the upper surface, of the electrode carrier which is directed toward the radially outer wall 44 of the cochlea. This phase of the insertion movement, which is effected by the surgeon pushing the positioning member longitudinally ahead, in the direction of the arrow A, with the aid of a suitable tool (not shown), results in the electrode carrier being effectively pulled along by the positioning member due to the presence of the joint 83. The forward movement of the assembly as a unit continues until the leading end region of the assembly comes into contact with the radially outer wall 44 of the cochlea, at which time a portion of the medial electrode-bearing region 81c of the electrode carrier is in contact with a portion of the radially inner wall 43 of the cochlea.

As the pushing force then continues to be exerted on the positioning member 82 by the surgeon, the assembly enters the spirally curved section of the cochlea and begins to adopt the curvature of the cochlea, with the upper surface of the positioning member gliding along the radially outer wall 44 of the cochlea as indicated in FIG. 7. At the same time, however, the frictional drag being exerted by the radially inner wall 43 of the cochlea on the electrode carrier tends to retard the movement of the electrode carrier somewhat relative to the movement of the positioning member. Thus, the continuing pushing force, still in the direction of the arrow A, that is exerted by the surgeon on the positioning member causes the trailing end region of the latter to advance somewhat relative to the electrode carrier past the location of the ring or band 89. As a result, by virtue of the connections 83 and 84 between the leading and trailing end regions of the electrode carrier and, respectively, the leading and trailing end regions of the positioning member and by virtue of the separation between the medial regions of the electrode carrier and the positioning member, the leading end region 82a of the positioning member begins curving away from the outer wall 44 of the cochlea. With the positioning member exerting an outwardly directed force on the radially outer wall of the cochlea, the leading end region of the electrode carrier is forced across the width of the scala tympani as the medial region of the positioning member between its leading end region and the part of its trailing end region then extending through the ring member 89 begins to assume an outwardly bowed or arched configuration relative to the medial region of the electrode carrier.

By the time the assembly has reached the end of the spiral section of the cochlea, therefore, as is indicated diagrammatically in FIG. 8, the forces exerted by the positioning member through its leading and trailing end regions on the corresponding end regions of the electrode carrier ensure that not only the leading and trailing end regions of the electrode carrier but also its medial region over substantially the entire length of its electrode-bearing lower surface are shifted across the scala tympani into close hugging contact with the radially inner wall 43 of the cochlea, thereby disposing the electrodes 85 in as close a juxtaposition to the modiolus and the ganglion cells 40 as possible. The positioning member thus not only achieves the desired disposition of the electrodes in proximity to the ganglion cells but also serves as the means for holding them in that disposition by virtue of the fact that the outward force exerted by the positioning member on the radially outer wall 44 of the cochlea ensures that the electrode carrier is continuously forced and held against the radially inner wall 43 of the cochlea.

Once the electrode carrier/positioning member assembly has been fully advanced into the cochlea to the desired final position of the electrode carrier, the ring member 89, which is then located just outside the entrance to the cochlea, becomes a means for locking the entire assembly in place within the cochlea. This is achieved automatically and without the surgeon having to perform any positive act toward that end. At that time, as shown in FIG. 8, the upward or outward inclination of the portion of the trailing end region 82b of the positioning member 82 located just forwardly of the ring member 89 ensures that the latter will exert a frictional restraining action on the positioning member, thereby inhibiting any reverse movement thereof. Thus, since the medial region of the positioning member cannot straighten out and must remain in substantially full surface contact over the major portion of its length with the radially outer wall of the cochlea, any instability or inadvertent movement of the assembly and especially of the electrode carrier in the cochlea is rendered effectively impossible.

Figure 9:
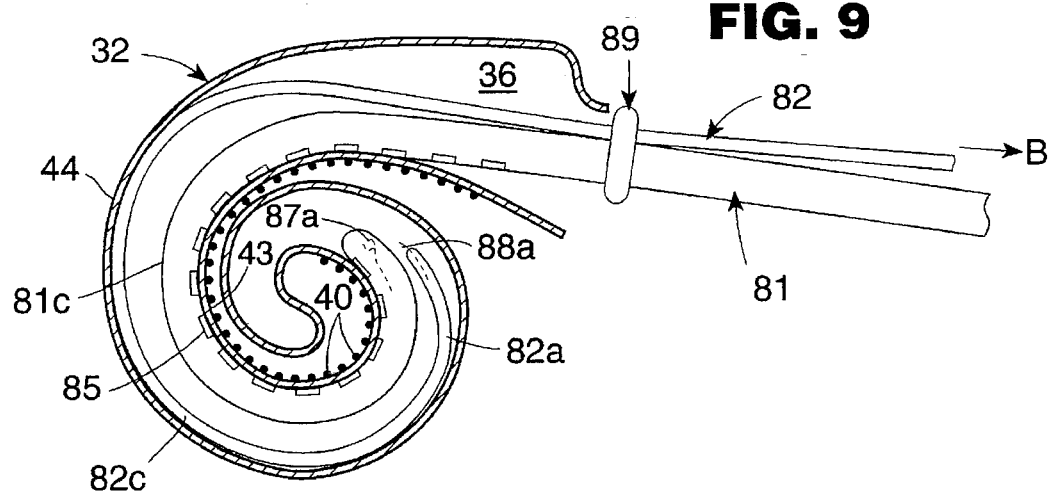
FIG. 9 is a schematic illustration, in longitudinal section, of the initial stage of the extraction of the positioning member from the patient's ear.
Figure 10:
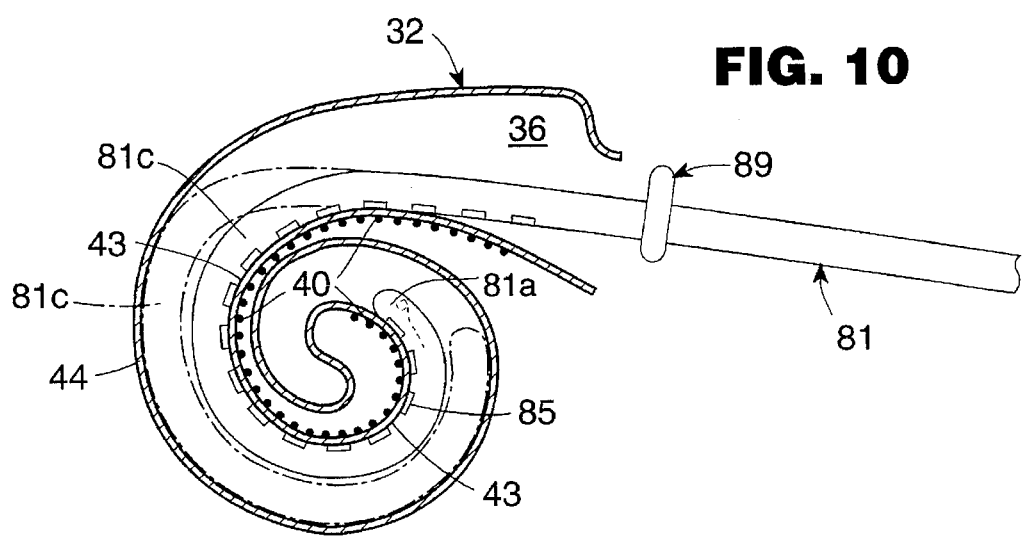
FIG. 10 is a similar view showing two possible positions of the electrode carrier after separation of the positioning member therefrom and preparatory to an extraction of the electrode carrier from the ear.

Referring now to FIGS. 9 and 10, the present invention greatly facilitates the removal of the implanted electrode assembly from the patient's ear if that becomes necessary for some reason. In that case, the surgeon needs only to hold the ring 89 stationary in the patient's outer ear and at the same time to exert on the positioning member 82 a rearwardly directed longitudinal pulling force, in the direction of the arrow B, of sufficient magnitude to overcome the frictional interaction between the ring and the obliquely inclined portion of the trailing end region of the positioning member. The resultant rearward sliding movement of that portion of the positioning member through the ring first straightens the arched portion of the positioning member down against the electrode carrier and ultimately causes the rod-part 88a of the joint 83 to be pulled freely out of the associated coil-shaped socket-part 87a of the joint. Thereafter, the then disconnected leading end region 82a and the medial region 82c of the positioning member move rearwardly along the radially outer wall 44 of the cochlea while in sliding contact with that wall, as shown in FIG. 9, which permits the positioning member to be easily withdrawn from the cochlea.

The immediate effect of this extraction of the positioning member on the electrode carrier 81 will then depend on whether or not scar tissue has grown in the cochlea and encapsulated the electrode carrier. If such encapsulation (not shown) has taken place, the electrode carrier will remain in its operational adjusted position, as shown in solid lines in FIG. 10, with the electrodes or contact elements 85 still in close proximity to the modiolus 43 and the ganglion cells 40. On the other hand, if no encapsulation has taken place, then after the connection 83 has been broken and the positioning member has been withdrawn, the "memory" of the material of which the electrode carrier is made causes the latter to try to uncoil and straighten out, with the result that the upper surface of the electrode carrier comes into contact with the radially outer wall of the cochlea, as shown in broken lines in FIG. 10. In either condition, of course, the electrode carrier can be easily extracted from the cochlea.

In summary, therefore, the self-positioning cochlear electrode implant assembly of the present invention which, like the assemblies disclosed in my aforesaid application Ser. No. 414,656, is designed for stimulating cells of the spiral ganglion in the scala tympani of the spirally curved cochlea of a human ear, includes the following basic features: (1) a rod-shaped cochlear electrode carrier which is made of a biocompatible plastic material and is sufficiently flexible to be able to assume the spiral curvature of the cochlea, and which has leading and trailing end regions and is tapered in cross-section from its trailing end region to its leading end region; (2) an array of cochlear electrode elements supported by the electrode carrier at respective longitudinally spaced locations thereon in a medial region of the electrode carrier between its leading and trailing end regions, the electrode elements having respective contact faces exposed along a first longitudinal side region, i.e., the lower surface, of the electrode carrier; (3) a rod-shaped positioning member for the electrode carrier, the positioning member being made of a biocompatible plastic material which has anti-friction properties and is somewhat stiffer than the material of which the electrode carrier is made, the positioning member being nevertheless sufficiently flexible to be able to assume the spiral curvature of the cochlea, and the positioning member having leading and trailing end regions and being juxtaposed to and extending lengthwise of the electrode carrier along a second longitudinal side region, i.e., the upper surface, of the latter opposite the first longitudinal side region thereof so as to have the leading and trailing end regions of the positioning member located adjacent the leading and trailing end regions, respectively, of the electrode carrier; and (4) means connecting the leading and trailing end regions of the positioning member to the leading and trailing end regions, respectively, of the electrode carrier so as to leave a medial region of the positioning member separated from the medial region of the electrode carrier and adapted to assume an arched configuration relative to the medial region of the electrode carrier; the arrangement being such that (5) upon insertion of the assembly into the scala tympani with the positioning member engaging and closely following the curvature of the radially outer wall of the cochlea and with the electrode carrier juxtaposed to and closely following the curvature of the positioning member, the latter by virtue of the two connections thereof to the electrode carrier assumes its arched configuration against the constraint of the radially outer wall of the cochlea and exerts a force on the electrode carrier at the leading and trailing end regions thereof to shift the electrode carrier into engagement at its first longitudinal side region with the radially inner wall of the cochlea so as to position the contact faces of the array of electrode elements in close proximity to the spiral ganglion cells of the cochlea, and that (6) the connection between the trailing end region of the electrode carrier and the trailing end region of the positioning member serves, when the insertion of the assembly into the cochlea has been completed and the positioning member is in its arched configuration, to stabilize the assembly in and lock the same against inadvertent reverse movement out of the cochlea.

The novel characteristics of the assembly of the present invention are that (7) the connection between the respective leading end regions of the positioning member and the electrode carrier is constituted by a rod-and-socket joint the interfitting rod-part and socket-part of which are not latchable to each other, and that (8) the connection between the respective trailing end regions of the positioning member and the electrode carrier is constituted by a band or ring member which is made of a biocompatible plastic material such as Silastic and surrounds and closely embraces both the positioning member and the electrode carrier in a common passageway therefor and has a cross-sectionally substantially D-shaped configuration with the flat wall of the "D" defining the inner circumferential boundary surface of the ring and thus the outer boundary wall of the passageway.

It will be understood that the foregoing description of a preferred embodiment of the present invention is for purposes of illustration only, and that the various structural and operational features and relationships herein disclosed are susceptible to a number of modifications and changes none of which entails any departure from the spirit and scope of the present invention as defined in the hereto appended claims.

I claim:

1. A self-positioning cochlear electrode implant assembly adapted to be implanted in the scala tympani of the spirally curved cochlea of a human ear for stimulating cells of the spiral ganglion, which assembly includes a rod-shaped cochlear electrode carrier made of a biocompatible plastic material and sufficiently flexible to be able to assume the spiral curvature of the cochlea, said electrode carrier having leading and trailing end regions and tapering in cross-section from said trailing end region to said leading end region; an array of cochlear electrode elements supported by said electrode carrier at respective longitudinally spaced locations thereon in a medial region of said electrode carrier between said leading and trailing end regions thereof, said electrode elements having respective contact faces exposed along a first longitudinal side region of said electrode carrier; a rod-shaped electrode carrier-positioning member made of a biocompatible plastic material and sufficiently flexible to be able to assume the spiral curvature of the cochlea, said positioning member having leading and trailing end regions and being juxtaposed to and extending lengthwise of said electrode carrier along a second longitudinal side region of the latter opposite said first longitudinal side region thereof so as to have said leading and trailing end regions of said positioning member located adjacent said leading and trailing end regions, respectively, of said electrode carrier; and means connecting said leading and trailing end regions of said positioning member to said leading and trailing end regions, respectively, of said electrode carrier so as to leave a medial region of said positioning member separated from said medial region of said electrode carrier and adapted to assume an arched configuration relative to said medial region of said electrode carrier, so that when said assembly is inserted into the scala tympani and said medial region of said positioning member has assumed said arched configuration against the constraint of the radially outer wall of the cochlea, said electrode carrier is in engagement at said first longitudinal side region thereof with the radially inner wall of the cochlea so as to position said contact faces of said array of electrode elements in close proximity to the spiral ganglion cells of the cochlea, and the connection between said trailing end region of said electrode carrier and said trailing end region of said positioning member serves to stabilize said assembly in and lock the same against inadvertent reverse movement out of the cochlea;

wherein the improvement comprises that:

said means connecting said leading end regions of said electrode carrier and said positioning member to each other comprises a latchless rod-and-socket joint including a rod-part supported by one of said positioning member and electrode carrier and a correspondingly configured socket-part supported by the other of said positioning member and electrode carrier, said socket part being constructed for slidingly receiving said rod-part without the two parts becoming latched to each other; and said means for connecting said trailing end regions of said electrode carrier and said positioning member to each other comprises a ring-shaped member made of a biocompatible plastic material and defining a passageway extending therethrough dimensioned for jointly accommodating said electrode carrier and said positioning member with a close fit; and said ring-shaped member has a cross-sectional configuration defining a circumferential boundary surface for said passageway which, when said positioning member is in said arched state thereof and in the absence of a longitudinally and rearwardly directed force of an appropriate magnitude externally applied by the surgeon to said positioning member, frictionally restrains said positioning member against inadvertent reverse movement through said ring-shaped member and out of the cochlea.

2. A cochlear electrode implant assembly according to claim 1, wherein said cross-sectional configuration of said ring-shaped member is generally D-shaped, with the flat wall of the "D" defining said circumferential boundary surface of said passageway.

3. A cochlear electrode implant assembly according to claim 1, wherein said socket-part of said joint is supported by said electrode carrier, and said rod-part of said joint is supported by said positioning member.

4. A cochlear electrode implant assembly according to claim 3, wherein said socket-part of said joint comprises a wire coil formation made of a biocompatible metallic material and embedded in said leading end region of said electrode carrier, said wire coil formation has an axis and an axial hollow interior for receiving said rod-part of said joint, and said axis of said wire coil formation is obliquely inclined within said electrode carrier rearwardly and upwardly in the direction from said first to said second longitudinal side region thereof; said electrode carrier is provided at said second longitudinal side region thereof with an access opening aligned and communicating with said hollow interior of said wire coil formation; said rod-part of said joint comprises a rod-shaped element made of a biocompatible metallic material and projecting forwardly from said leading end region of said positioning member, and said rod-shaped element is obliquely inclined relative to said positioning member forwardly and downwardly in the direction from said positioning member toward said electrode carrier when the same are located adjacent each other in said assembly; and said joint is established by said rod-shaped element slidingly entering said hollow interior of said wire coil formation through said access opening, whereby only a forward movement of said positioning member causes a pushing force to be exerted by said rod-shaped element on said wire coil formation so as to cause a forward movement of said electrode carrier, while a rearward movement of said positioning member causes said rod-shaped element to be withdrawn from said wire coil formation and leaves said electrode carrier stationary.

5. A cochlear electrode implant assembly according to claim 4, wherein said positioning member has a guide wire embedded therein and extending through the entire length of said positioning member, the body of said guide wire within said positioning member is substantially flat in cross-sectional configuration and has a flat face thereof facing toward said second longitudinal side region of said electrode carrier when said positioning member and said electrode carrier are located adjacent each other in said assembly, said guide wire thereby stiffening said positioning member against flexure in a direction in the plane of said guide wire while permitting unhindered flexure of said positioning member in a direction perpendicular to the plane of said guide wire, and said rod-shaped element is constituted by an end region of said guide wire located outside said positioning member.

6. A cochlear electrode implant assembly according to claim 5, wherein the width of said body of said guide wire is about one-half the width of said positioning member in a side region of the latter which is located proximate to said second longitudinal side region of said electrode carrier when said positioning member and said electrode carrier are adjacent each other in said assembly.

7. A cochlear electrode implant assembly according to claim 5, wherein the portion of said guide wire which constitutes said rod-shaped element is of conventionally round cross-sectional configuration.

* * * * *